US009513228B2

(12) United States Patent
Shibata et al.

(10) Patent No.: US 9,513,228 B2
(45) Date of Patent: Dec. 6, 2016

(54) DEFECT INSPECTION METHOD AND ITS DEVICE

(71) Applicant: Hitachi High-Technologies Corporation, Minato-ku, Tokyo (JP)

(72) Inventors: Yukihiro Shibata, Tokyo (JP); Kei Shimura, Tokyo (JP); Sachio Uto, Tokyo (JP); Toshifumi Honda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/377,753

(22) PCT Filed: Oct. 22, 2012

(86) PCT No.: PCT/JP2012/077250
§ 371 (c)(1),
(2) Date: Aug. 8, 2014

(87) PCT Pub. No.: WO2013/136574
PCT Pub. Date: Sep. 19, 2013

(65) Prior Publication Data
US 2015/0022806 A1  Jan. 22, 2015

(30) Foreign Application Priority Data

Mar. 13, 2012 (JP) ................................ 2012-055362

(51) Int. Cl.
*G01N 21/00* (2006.01)
*G01N 21/94* (2006.01)
(Continued)

(52) U.S. Cl.
CPC .......... *G01N 21/94* (2013.01); *G01N 21/8806* (2013.01); *G01N 21/8851* (2013.01); *G01N 21/9501* (2013.01); *G01N 21/956* (2013.01);
(Continued)

(58) Field of Classification Search
USPC ...................... 356/237.1–237.6, 239.1–239.8
See application file for complete search history.

(56) References Cited

U.S. PATENT DOCUMENTS 6,608,676 B1* 8/2003 Zhao et al. ................ 356/237.2
2005/0219518 A1* 10/2005 Korngut ................. G01N 21/47
356/237.2

(Continued)

FOREIGN PATENT DOCUMENTS

| JP | 05-209841 A | 8/1993 |
| JP | 2011-013077 A | 1/2011 |
| JP | 2012-032252 A | 2/2012 |
| WO | WO 99/06823 A1 | 2/1999 |

*Primary Examiner* — Tri T Ton
(74) *Attorney, Agent, or Firm* — Miles & Stockbridge P.C.

(57) ABSTRACT

To increase the illumination efficiency by facilitating the change of the incident angle of illumination light with a narrow illumination width according to an inspection object and enabling an illumination region to be effectively irradiated with light, provided is a defect inspection method for obliquely irradiating a sample mounted on a table that is moving continuously in one direction with illumination light, collecting scattered light from the sample obliquely irradiated with the illumination light, detecting an image of the surface of the sample formed by the scattered light, processing a signal obtained by detecting the image formed by the scattered light, and extracting a defect candidate, wherein the oblique irradiation of the light is implemented by linearly collecting light emitted from a light source, and obliquely projecting the collected light onto the surface of the sample, thereby illuminating a linear region on the surface of the sample.

20 Claims, 7 Drawing Sheets

(51) Int. Cl.
*G01N 21/956* (2006.01)
*G01N 21/95* (2006.01)
*G03F 7/20* (2006.01)
*G01N 21/88* (2006.01)
*G01N 21/958* (2006.01)

(52) U.S. Cl.
CPC ........... *G01N 21/958* (2013.01); *G03F 7/7065* (2013.01); *G01N 2021/8822* (2013.01); *G01N 2201/068* (2013.01); *G01N 2201/0697* (2013.01); *G01N 2201/06113* (2013.01)

(56) References Cited

U.S. PATENT DOCUMENTS

| | | |
|---|---|---|
| 2006/0274432 A1 | 12/2006 | Jeong |
| 2009/0059216 A1* | 3/2009 | Shibata et al. ............. 356/237.4 |
| 2009/0279081 A1* | 11/2009 | Urano et al. ............... 356/237.5 |
| 2010/0014075 A1* | 1/2010 | Ueno et al. ................ 356/237.5 |
| 2010/0225903 A1* | 9/2010 | Nishiyama et al. ....... 356/237.2 |
| 2012/0092484 A1 | 4/2012 | Taniguchi et al. |
| 2013/0141715 A1 | 6/2013 | Urano et al. |

\* cited by examiner

DEFECT INSPECTION METHOD AND ITS DEVICE

BACKGROUND

The present invention relates to a defect inspection method which optically inspects defects of a minute pattern or foreign matters formed on a sample through a thin film process typically included in a semiconductor manufacturing process or a flat panel display manufacturing process, and more particularly to a defect inspection method and its device including an illumination optical system which is suitable for detecting the minute defects or foreign matters.

WO 1999/006823 A (Patent Literature 1) discloses a conventional semiconductor wafer inspection device. This patent literature discloses a system for illuminating a laser beam linearly onto a wafer. As the illumination system, in the disclosed technique, the cylindrical lens or the main surface of the mirror is arranged, parallelly to the wafer, and the wafer is illuminated in a linear pattern.

JP 5-209841 A (Patent Literature 2) discloses a system for linearly illuminating the wafer. The literature discloses a technique for condensing a laser beam onto a diffraction grating and obliquely forming an image of the condensed light.

CITATION LIST

Patent Literature

Patent Literature 1: JP 1999/006823 A
Patent Literature 2: JP 5-209841 A

SUMMARY

In the example of a target semiconductor wafer to be inspected, there are different numbers of layers of a multilayer structure, different wiring materials in layers, different widths or forms of the pattern, and different processing steps for forming the pattern, in accordance with a variety of products (memory product or logical product) or the generation of the wiring node. Thus, there are a wide variety of defects to be detected. Typical examples of defects includes short-circuit or open-circuit in the same layer or different layers (interlayer wiring).

To detect the defects with high sensitivity, it is necessary to detect an image with a visualized defect image and to perform a defect determination image process. To detect an image in which there is a high contrast of the defect image, it is necessary to adjust illumination conditions and detecting conditions, in accordance with target defects to be detected.

Adjustment parameters as illumination conditions in a device having a laser as a light source include an incidence angle, direction, polarization, and line width of the illumination. The line width is preferably very minute, and the conditions for actualizing the defect image are different in accordance with the above-described defect type (variety), in relation to another incidence angle, direction, and polarization. Thus, it is preferred to set the illumination conditions corresponding to targets defect to be detected in each manufacturing process for wafer.

Patent Literature 1 discloses that a cylindrical lens or a cylindrical mirror is arranged, and light is condensed and illuminated above the wafer. When the width of light condensing illumination is minute, that is, in a range from 1 to 2 μm or smaller than that, it is necessary to sufficiently restrain the wavefront aberration in the light condensing illumination. Thus, the curvature or thickness of the cylindrical lens or mirror needs to correspond to a particular incidence angle or direction. To realize the configuration in which the incidence angle is changed to, for example, 60 degrees or 70 degrees, in accordance with the target object to be inspected, it is necessary to realize a configuration which includes a replaceable cylindrical lens or mirror, in accordance with the incidence angle. To realize the width of the condensing light in a range 1 to 2 μm or smaller than that, it is necessary to remarkably enhance the profile irregularity of the lens or mirror or the positioning accuracy at the replacement. At this time, a problem is that it takes quite a longtime to replace the cylindrical lens or mirror.

Patent Literature 2 does not disclose a technique for changing the incidence angle or direction of the illumination.

In Patent Literature 1, in the configuration using the cylindrical lens or mirror, a light beam in a direction orthogonal to the plane of incidence with respect to the lens or mirror is not condensed onto one point of the wafer and is spread into the direction of the plane of incidence, when a circular laser beam with a Gaussian distribution obliquely enters a cylindrical lens or mirror to illuminate above the wafer. The spread is equal to or greater than 5 to 10 nm, when the illumination conditions are: the light condensing width is 1 to 2 μm, the wavelength is 355 nm, and the incidence angle is 70 degrees. Thus, the actual illumination is in a range from 5 to 10 nm, even if the required illumination range is set to 1 to 2 mm, thus lowering the illumination intensity in the required illumination range. To avoid lowering of the inspection speed due to the lowering of the illumination, a problematic subject is that an expensive high output laser needs to be used.

The present invention aims to solve the problem of the conventional technique and to provide an illumination method and a defect inspection device using the method, for facilitating changing of an incidence angle of illumination light with a narrow illumination width in accordance with a target to be inspected and for enhancing the illumination efficiency by efficiently irradiating illumination light into an illumination range.

To solve the above-described object, according to the present invention, there is provided a defect inspection device comprising: a table unit on which a target sample to be inspected is mounted; an illumination optical system unit configured to obliquely illuminate the sample mounted on the table unit; a detecting optical system unit which condenses scattered light generated from the sample on which illumination light is obliquely irradiated by the illumination light optical system unit, and detects an image on a surface of the sample using the scattered light; an image processing unit configured to process a signal obtained by detecting the image on the surface of the sample using the scattered light by the detecting optical system unit, to extract defect candidates on the surface of the sample; and a control unit which controls the table unit, the illumination optical system unit, the detecting optical system unit, and the image processing unit, and wherein the illumination optical system unit includes a laser light source which emits a laser beam; a beam expander which expands a diameter of the laser beam, an anamorphic optical unit which controls a size of the laser beam in a particular direction; a cylindrical optical unit which condenses the laser beam passed through the anamorphic optical unit in one direction and forms a linearly condensed light image as an intermediate image; and a relay lens unit which forms the linearly condensed light image on a surface of the specimen mounted on the table unit to illuminate a linear region on the specimen, wherein a polarization condition of the laser beam passing through the anamorphic optical unit and the cylindrical optical unit is a specific linearly polarized condition, wherein optical coatings are applied to surfaces of a cylindrical lens of the cylindrical optical unit, said optical coating corresponding to the polarization state of the laser beam to reduce power loss of the laser beam, and wherein the relay lens unit includes a polarization control element which controls polarization condition of the laser beam illuminating the specimen.

The solve the above-described object, according to the present invention, there is provided a defect inspection method comprising the steps of: irradiating illumination light obliquely onto a sample mounted on a table which is continuously moved in one direction; detecting an image on a surface of the sample using scattered light, by condensing the scattered light generated on the sample onto which the illumination light is obliquely irradiated; and processing a signal obtained by detecting the image on the surface of the sample using the scattered light to extract defect candidates on the surface of the sample, and wherein the irradiating the illumination light obliquely onto the sample includes illuminating a linear region of the surface of the sample, by forming an image of condensed light by linearly condensing light emitted from a light source, projecting the image of the condensed light obliquely onto the surface of the sample mounted on a table which is moved continuously in one direction, and forming the image on the surface of the sample.

According to the present invention, the line width of the illumination can be minutely formed, in a range from 1 to 2 μm or lower, and it is possible to adjust the incidence angle, direction, and polarization of illumination light in relation to each target defect to be inspected. As a result, it can be expected to improve the inspection sensitivity by actualizing a defect image with a very minute defect. Further, it is possible to set a plurality of illumination incidence angles without changing to an expensive condensing mirror or lens, thus restraining the cost for the device. The light output from the laser can be formed with low loss and without spreading the illumination range more than necessary. Therefore, relatively a low output laser is applicable, and it is possible to realize low cost of laser and suppress damage on illumination components.

DESCRIPTION OF THE PREFERRED EMBODIMENTS

Preferred embodiments of the present invention will now be described using the drawings.

First Embodiment

Figure 1:
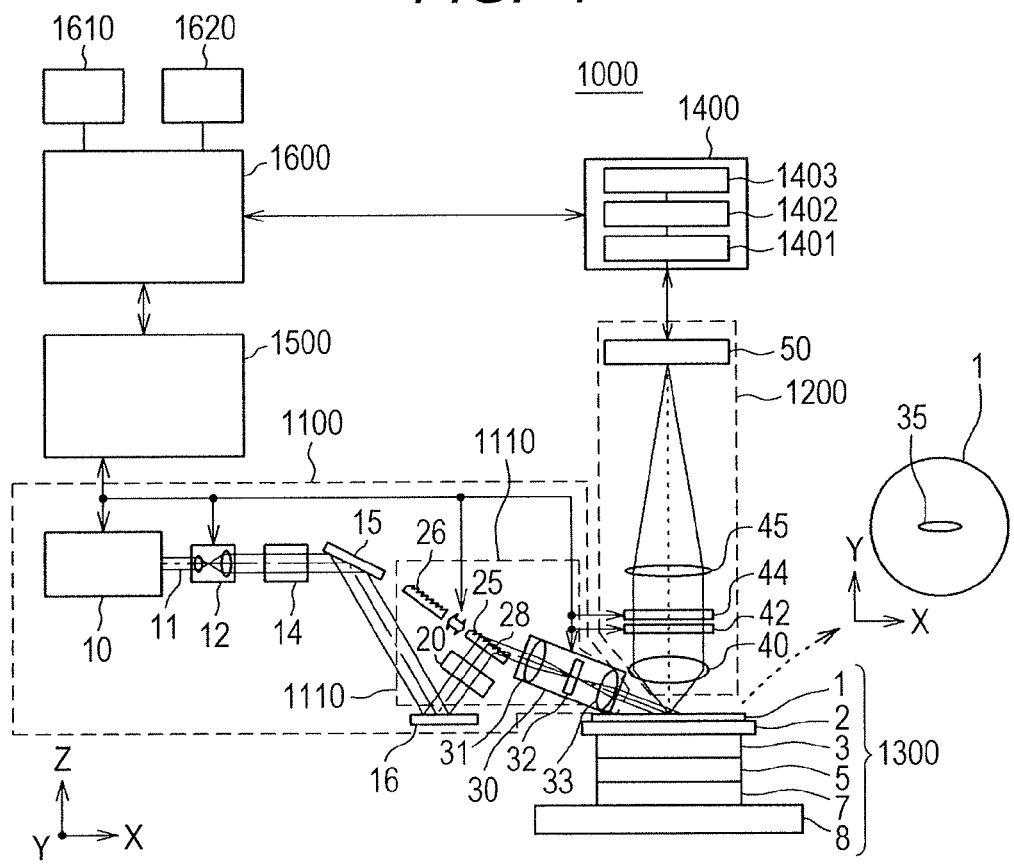
FIG. 1 is a block diagram illustrating a schematic configuration of a defect inspection device in a first embodiment.

Descriptions will now be made to an example in which the present invention is applied to a defect inspection device 1000 which inspects defects, such as a short-circuit defect, an open defect, or a foreign matter defect of the pattern of a semiconductor wafer, using any FIG. 1 to FIG. 5. FIG. 1 illustrates a configuration of the defect inspection device 1000.

The defect inspection device 1000 includes a stage unit 1300, an illumination optical system 1100, a detecting optical system 1200, an image processing unit 1400, a mechanism control unit 1500, a system control unit 1600, a storage unit 1610, and a display unit 1620. The stage unit 1300 is provided for placing thereon a semiconductor wafer (hereinafter referred to as a wafer) 1 having a circuit pattern on a target surface to be inspected, and is movable in an X-Y plane and in a height direction (Z direction). The illumination optical system 1100 irradiates illumination light to the wafer 1 placed on the stage unit 1300. The detecting optical system 1200 detects scattered light from the wafer 1 to which the illumination light is irradiated. The image processing unit 1400 processes a scattered light detecting signal from the wafer 1, output from the detecting optical system 1200. The mechanism control unit 1500 controls operations of the mechanism units of the illumination optical system 1100, the detecting optical system 1200, and the stage unit 1300. The system control unit 1600 controls the image processing unit 1400 and the mechanism control unit 1500. The storage unit 1600 stores inspection results and inspection conditions. The display unit 1620 includes a screen for inputting the inspection conditions and displaying the inspection results.

The illumination optical system 1100 includes a laser light source 10, a beam expander 12, an anamorphic prism 14, a mirror 15, and a beam irradiation unit 1110. The beam expander 12 expands the beam diameter of a laser emitted from the laser light source 10. The anamorphic prism 14 expands the laser beam expanded by the beam expander 12 into a particular direction. The mirror 15 reflects the laser beam emitted from the anamorphic prism 14 to change the optical path. The beam irradiation unit 1110 irradiates the laser beam whose optical path has been changed by the mirror 15 to the wafer 1 placed on the stage unit 1300, from an oblique direction toward an elongated region (linear region) 35 thereof. A configuration of the beam irradiation unit 1110 will specifically be described later.

The stage unit 1300 includes a chuck 2, a Z stage 3, an X stage 5, a Y stage 7, and a base plate 8. The chuck 2 absorbs to chuck and holds the wafer 1. The Z stage 3 is provided for placing thereon the chuck 2 and movable in a height direction (Z direction). The X stage 5 is provided for placing the Z stage 3 thereon and movable in an X direction in a plane. The Y stage 7 is provided for placing the X stage 5 thereon and movable in a Y direction in a plane. The base plate 8 is provided for placing the Y stage 7 thereon. The stage unit 1300 further includes a position sensor which detects the positions of the Z stage 3, the X stage 5, and the Y stage 7, and no illustration thereof is given.

The detecting optical system 1200 includes an objective lens 40, a spatial filter 42, a polarizing filter 44, an imaging lens 45, and an image sensor 50. The objective lens 40 captures and condenses light scattered above the wafer 1, of scattered light generated from the region 35 illuminated by the illumination optical system 1100, in the wafer 1 held by the chuck 2 of the stage unit 1300. The spatial filter 42 shields the strong diffraction light generated by the light scattered from fine repetitive patterns formed on the wafer 1, of the scattered light from the wafer 1 as captured by the objective lens 40. The polarizing filter 44 transmits only a specific polarization, of the scattered light from the wafer 1 that has passed through the spatial filter 42 without being shielded by the spatial filter 42. The imaging lens 45 is provided for imaging the specific polarization transmitted through the polarizing filter 44. The image sensor 50 detects the image of the scattered light, as imaged by the imaging lens 45.

The image processing unit 1400 includes an A/D conversion unit 1401, a signal processing unit 1402, and a defect detecting unit 1403. The A/D conversion unit 1401 amplifies a detection signal (an analog signal) output from the image sensor 50, and converts it into a digital signal (A/D conversion). The signal processing unit 1402 processes the A/D converted signal to acquire an image signal. The defect detecting unit 1403 processes the image signal acquired by the signal processing unit 1402, extracts defect candidates, and obtains an image feature amount of the extracted defect candidate.

The defect inspection device 1000 including the above configuration is used for inspecting defects on the surface of the semiconductor wafer 1 having the circuit pattern formed thereon.

The semiconductor wafer 1 as a target to be inspected is absorbs to chuck by the chuck 2. This chuck 2 is placed on the Z stage 3 which mounts on the X stage 5 and the Y stage 7. The entire surface of the wafer 1 is inspected by the horizontal movement of the X stage 5 and the Y stage 7.

The laser light source 10 of the illumination optical system 1100 may be of a type that outputs a continuous wave laser or a type that outputs a pulsed laser. Candidates of the laser light source 10 include those having wavelengths of 532 nm, 355 nm, 266 nm, and gas lasers with 248 nm (KrF), 193 nm (ArF), 157 nm (F2).

A laser beam 11 oscillated by the laser light source 10 is expanded by the beam expander 12 into a predetermined beam diameter, and expanded by the anamorphic prism 14 only in a particular direction, to be formed in an elliptic light flux. In this case, the particular direction implies a condensed direction on the wafer 1.

Figure 2A:
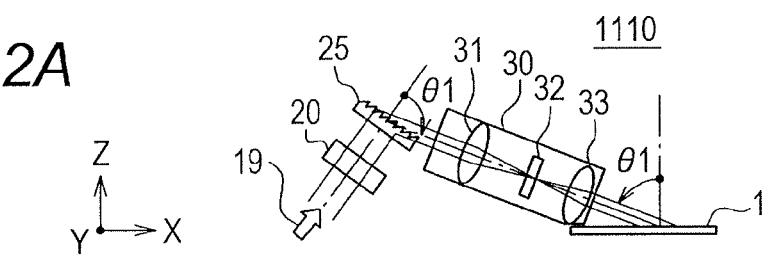
FIG. 2A is a block diagram illustrating a configuration of a beam irradiation unit, in which a diffraction grating with relatively a narrow grating pitch is used, in the first embodiment.

The laser beam 11 formed as the elliptic light flux is reflected on planar mirrors 15 and 16, and enters the beam irradiation unit 1110. As illustrated in FIG. 2A, the laser beam of the elliptic light flux which has entered the beam irradiation unit 1110 enters the cylindrical lens 20, and is condensed in the form of a narrow light flux on a transmission diffraction grating 25. To reduce the aberration in the condensing unit and to have a narrower width of the condensed light, the convex surface of the cylindrical lens 20 preferably has an aspherical surface form. The laser beam 11 emitted from the cylindrical lens 20 enters the transmission diffraction grating 25, and its incidence angle may be any of 0° angle of incidence as perpendicular illumination or an oblique angle.

Of the laser beam 11 entering the transmission diffraction grating 25, particular high-order diffracted light 28 diffracted by the transmission diffraction grating 25 enters a relay lens 30 including lenses 31 and 33, and a linear condensing line formed by the narrow light flux condensed on the surface of the transmission diffraction grating 25 obliquely enters the wafer 1, to form an image on the longitudinal in the X direction of the wafer 1 and in the narrow region (linear region) 35 in the Y direction thereof. The relay lens 30 is a both-side telecentric relay lens. The illumination light irradiated onto the linear region 35 of the wafer 1 is longitudinal in the X direction. The relay lens 30 is set in a manner that the surface of the wafer 1 and the transmission diffraction grating 25 are in a conjugate relationship. The light condensed in the form of a narrow light flux on the surface of the transmission diffraction grating 25 is projected in the linear region of the 35 on the wafer. Therefore, it is possible to illuminate the wafer 1 with the linearly condensed light.

It is preferred to set the angle of the laser beam 11 entering the transmission diffraction grating 25 after transmitting through the cylindrical lens 20 is set to an angle at which the diffraction efficiency of the particular high-order diffracted light 28 for use in the illumination will be high. When the magnification of the relay lens 30 is equal magnification, the number of grating members (or grating pitch) per unit length of the transmission diffraction grating 25 may be set in a manner that the angle of the high-order diffracted light from the normal line of the diffraction grating coincides with the angle of incidence on the wafer 1. To change the angle of incidence on the wafer 1, a non-illustrative driving unit is used for changing the transmission diffraction grating 25 to the transmission diffraction grating 26 which has different number of gratings (or grading pitch) of the diffraction gratings per unit length.

Further, generally, in the diffraction grating, the grating efficiency is changed in accordance with the polarization. As this diffraction efficiency is high, the efficiency for light utilization as an illumination system is increased. It is therefore possible to apply the light source which oscillates an inexpensive low-output laser, as the laser light source 10. To acquire the maximum diffraction efficiency, the incident polarization of light to the transmission diffraction grating 25 may be any of S polarization and P polarization. The P or S polarization light which has been adjusted to obtain the maximum diffraction efficiency is assumed as the incidence polarization light for the diffraction grating. However, to visualize the defects generated on the wafer 1, it is necessary to be able to change the polarization state of the light between S/P/circular polarization in accordance with the defect type.

Therefore, a wavelength plate 32 is embedded between the lenses 31 and 33 which form the relay lens 30 arranged between the transmission diffraction grating 25 and the wafer 1. The plate 32 is formed of a ½ wavelength plate, a ¼ wavelength plate, or a combination thereof, which is independently rotatable. The grating pitch of the diffraction grating 25 is set equal to or smaller than the resolution of the relay lens 30. As a result, it is possible to reduce the light and darkness occurring in the illumination light irradiated in the linear region 35 on the wafer 1. The light and darkness is due to the periodic structure of the transmission diffraction grating 25.

With the objective lens 40, the detecting optical system 1200 captures light scattered above the wafer 1, of light scattered by the pattern or defects formed in the linear region 35 of the wafer 1, using illumination light irradiated in the linear region 35 on the wafer 1. The system 1200 shields the diffracted light from the normal pattern by the light shielding pattern formed in the spatial filter 42 arranged in the Fourier transform region of the objective lens 40. Of light transmitted through the spatial filter 42, light having a particular polarized component transmits through the polarizing filter 44. Then, a dark field image of the wafer 1 is formed on the image sensor 50, by the imaging lens 45.

Candidates of the image sensor 50 are of a CCD (Charge Coupled Device) type or a CMOS (Complementary Metal Oxide Semiconductor) type. The configuration illustrated in FIG. 1 is that of the one-dimensional image sensor which continuously detects images while scanning the Y stage 7 with uniform speed. This one-dimensional image sensor 50 may be a plural-line sensor, such as a TDI (Time Delay Integration) sensor, a dual line sensor, and the like.

The image processing unit 1400 amplifies an analog signal output from the image sensor 50 which has detected the dark field image of the wafer 1, using the A/D conversion unit 1401, and converts it into a digital signal (A/D conversion). Then, the A/D converted digital signal is input to the signal processing unit 1402 and image-processed, thereby obtaining a digital image. This digital image is sent to the defect detecting unit 1403, and is image-processed (including die comparison or cell comparison), thereby extracting defect candidates and calculating an image feature amount of the extracted candidates. The position information of the defect candidates and information regarding the image feature amount are sent to the system control unit 1600.

The system control unit 1600 displays a GUI (Graphical User Interface) with the user who instructs the defect inspection device 1000 for an operation, on the display screen of the display unit 1620. Thus, it is possible to browse information regarding defects that the user would like to detect, through the GUI, and also a past inspection history or inspection recipe stored in the storage unit 1610. The information sent from the image processing unit 1400 is stored in the storage unit 1610. Each mechanism operates in response to an instruction made by the user through the GUI displayed on the display unit 1620, through the mechanism control unit 1500. The mechanisms to be controlled include the ON/OFF of the laser light source 10 of the illumination optical system 1100, the expansion ratio of the beam expander 12, the exchange of the transmission diffraction grating 25, the rotation angle of the wavelength plate unit 32, the shielding pattern of the spatial filter 42 of the detecting optical system 1200, the rotation angle of the polarization filter 44, and the instruction for the operation of each stage of the stage unit 1300 or timing to capture images into the image processing unit 1400.

Figure 2B:
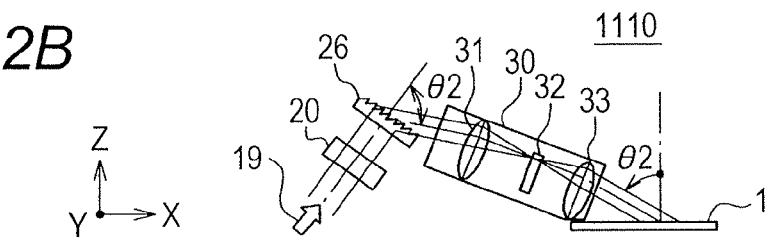
FIG. 2B is a block diagram illustrating a configuration of a beam irradiation unit, in which a diffraction grating with relatively a wide grating pitch is used, in the first embodiment.

FIG. 2A and FIG. 2B illustrate the scheme to change the illumination incidence angle onto the wafer 1 by switching the transmission diffraction gratings 25 and 26 using a non-illustrative switching mechanism, in the beam irradiation unit 1110. In FIG. 2A, a laser beam 19 enters the cylindrical lens 20, transmits through the cylindrical lens 20, and then is linearly condensed on the transmission diffraction grating 25. In the laser beam 19, the cross sectional shape of the optical axis is formed as an ellipse. Of the light transmitted through the transmission diffraction grating 25, the angle of θ1 is set between the high-order diffracted light diffracted on the side of the relay lens 30 and for use in the illumination and the normal line of the transmission diffraction grating 25. An equal magnification relay system 30 causes a condensed light image of the laser beam 19 to obliquely enter the wafer 1 at the incidence angle θ1, to form an image (oblique projection) in the linear region 35 on the wafer 1. Note that this image of the laser is one that has linearly been condensed on the transmission diffraction grating 25.

FIG. 2B illustrates a configuration in which the incidence angle to the wafer 1 is made smaller than that of FIG. 2A. The laser beam 19, the cylindrical lens 20, the relay lens 30, and the wafer 1 are arranged in the same manner as that of FIG. 2A, while the transmission diffraction grating 25 used in FIG. 2A is replaced with the transmission diffraction grating 26 having a larger pitch than that of the transmission diffraction grating 25.

Let it be assumed that the angle formed by the incidence laser beam 19 and the normal line of the diffraction grating is "α" and the angle (angle of diffraction) formed between the diffracted light and the normal line of the diffraction grating is "β". In this case, the following relational expression can be used.

$$\sin\alpha \pm \sin\beta = Nm\lambda \quad \text{(Expression 1)}$$

N: number of grating members per mm
m: degree of diffraction (m=0, ±1, ±2, ... )
λ: wavelength The transmission diffraction grating 26 illustrated in FIG. 2B includes a less number of grating members than that of the transmission diffraction grating 26 illustrated in FIG. 2A, (that is, there is a large pitch between the grating members).

If the angle of diffraction β gets smaller, the angle θ2 formed between the high-order diffraction light and the normal line of the diffraction grating 26 becomes smaller than θ1. By performing oblique projection on the wafer 1 with the relay lens 30 designed with an NA (Numerical Aperture) for enabling to capture the high-order diffracted light, it is possible to illuminate the wafer 1 at a large incidence angle as compared to the case of FIG. 2A.

Accordingly, the image of the condensed laser beam 19 which has linearly been condensed by the cylindrical lens 20 is formed in the linear region 35 on the wafer 1. Thus, if an image of condensed light with a width equal to or narrower than 1 to 2 μm can be formed, the linear region 35 to be formed on the wafer 1 can have a width equal to or narrower than 1 to 2 μm, regardless of the incidence angle of the illumination light onto the wafer 1. It is possible to avoid diffusion of illumination light to a region, beyond an imaging range for inspection and thus having nothing to do with inspection. Therefore, the laser beam 11 output from the laser light source 10 can be irradiated with high efficiency onto a target range to be inspected on the wafer 1, that is, on the imaging range for inspection. As a result, it is possible to improve the illumination brightness of the linear region having a narrow line width on the wafer 1, thus enabling to perform high sensitive inspection.

By changing the pitch of the diffraction pattern in the transmission diffraction grating, it is possible to change the incidence angle of the high-order diffracted light from the transmission diffraction grating onto the wafer 1, without changing the positions of the illumination optical system 1100 and/or the beam irradiation unit 1110.

Figure 3:
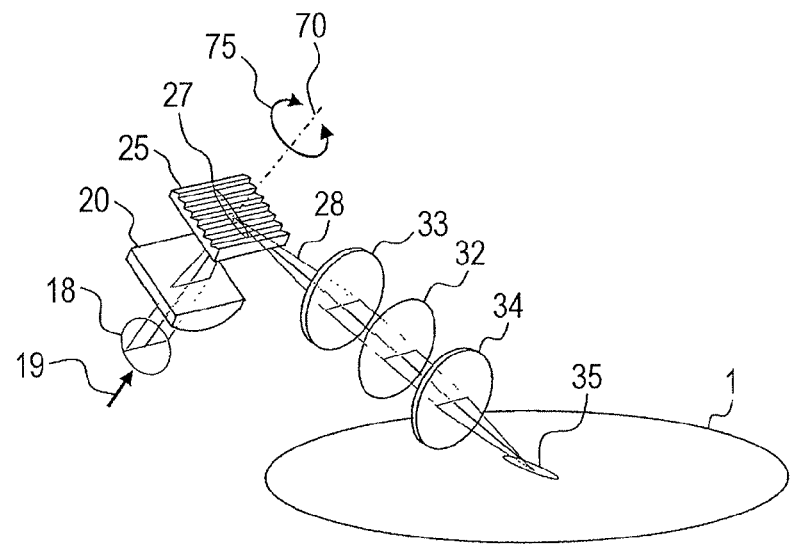
FIG. 3 is a perspective view of the beam irradiation unit, illustrating the scheme of the irradiation incidence angle and the change of the direction by in-plane rotation of the diffraction grating, when an image of light condensed by a cylindrical lens is formed on the grating plane of the diffraction grating, in the first embodiment.

FIG. 3 illustrates a unit for changing the illumination elevation angle and the direction for the wafer 1. The laser beam 19 entering the cylindrical lens 20 is parallel light, and has a cross sectional shape which is formed as an ellipse 18 by the anamorphic prism 14. This cross sectional shape is in a plane perpendicular to the optical axis. The parallel light is linearly condensed 27 on the transmission diffraction grating 25 by the cylindrical lens 20. Of the diffracted light generated by the laser beam 19 transmitting through the cylindrical lens 20, the high-order diffracted light 28 is caused to enter the relay lens 30, and an image of the illumination light 27 is formed with an equal magnification. This illumination light is linearly condensed on the transmission diffraction light 25 on the wafer 1 by the lenses 31 and 33 included in the relay lens 30. In this configuration, it is possible to change the diffraction direction of the high-order diffraction light 28, by rotating the transmission diffusion grating 27 using a non-illustrative driving unit as shown with an arrow 75, at a grating normal line 70 as the rotational center. As a result, it is possible to control the illumination direction of the region 35 to which the illumination light is illuminated on the wafer 1, within the range of the NA of the lenses 31 and 33 included in the relay lens 30.

Figure 4:
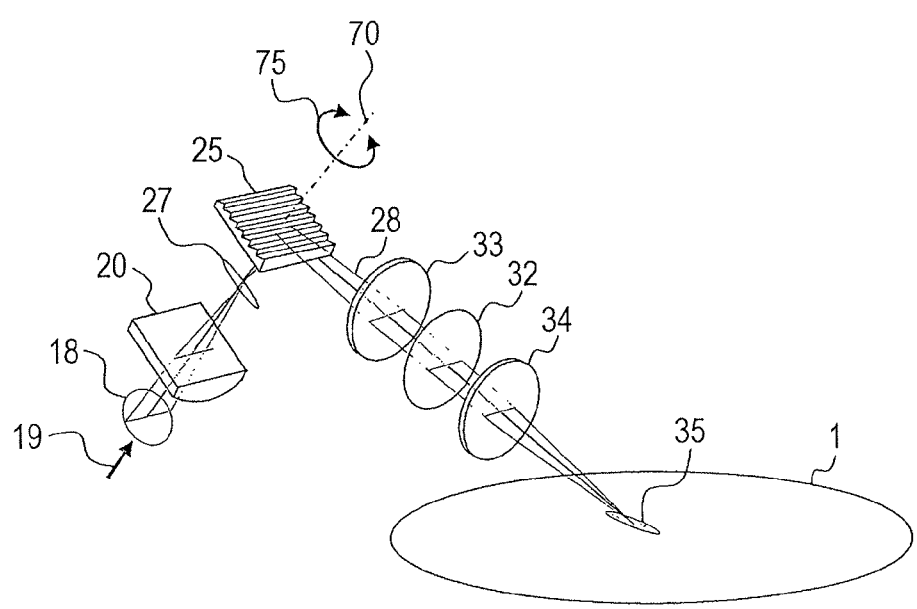
FIG. 4 is a perspective view of the beam irradiation unit, illustrating the scheme of the irradiation incidence angle and the change of the direction by in-plane rotation of the diffraction grating, when an image of light condensed by a cylindrical lens is formed in front of the diffraction grating, in the first embodiment.

In FIG. 1 to FIG. 3, the descriptions have been made to the configuration in which the condensed position of the laser entering the cylindrical lens 20 is adjacent to the grating plane of the transmission diffraction grating 27. However, it is possible to obliquely form a linear condensed light image on the wafer 1, as long as an imaging relation is kept between the condensed position 27 and the wafer 1, even if there is a certain distance equal to or greater than the depth of focus of the cylindrical lens 20 between the linearly-condensed position 27 by the cylindrical lens 20 and the transmission diffraction grating 25, as illustrated in FIG. 4. Accordingly, the condensed position and the grating plane are spatially separated, thereby enabling to reduce the energy of the laser beam condensed on the grating plane and to restrain the damage on the grating plane of the transmission diffraction grating 25.

Figure 5:
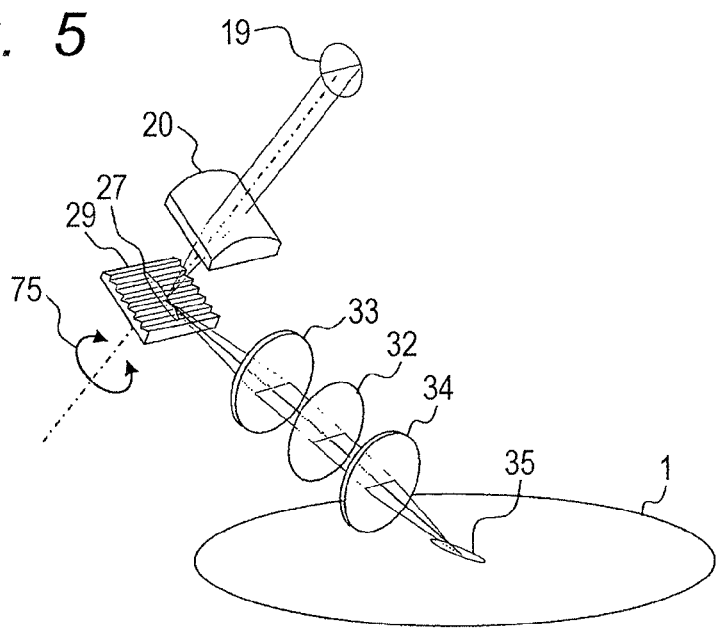
FIG. 5 is a perspective view illustrating a configuration of the beam irradiation unit, when a reflection type diffraction grating is used as a diffraction grating, in the first embodiment.

In FIG. 1 to FIG. 4, the descriptions have been made to the example in which the transmission diffraction grating 25 is used as a diffraction grating. FIG. 5 illustrates an example in which a reflection diffraction grating 29 is used in place of the transmission diffraction grating 25. In the configuration illustrated in FIG. 5, the cylindrical lens 20 is arranged on the side of the plane where the diffraction grating of the reflection diffraction grating 29 is formed. In addition, the laser beam 19 which is formed as an ellipse by the anamorphic prism 14 and reflected on the mirror 15 is caused to enter the cylindrical lens 20, without using the mirror 16 included in the configuration of FIG. 1, and is linearly condensed 27 near the reflection diffraction grating 29. In the configuration, the high-order reflected light for use in illumination is condensed to obliquely form an image of condensed light near the reflection diffraction grating 29, in the linear region 35 on the wafer 1, using the lenses 31 and 33 included in the equal magnification relay system of the relay lens 30.

Second Embodiment

Figure 6:
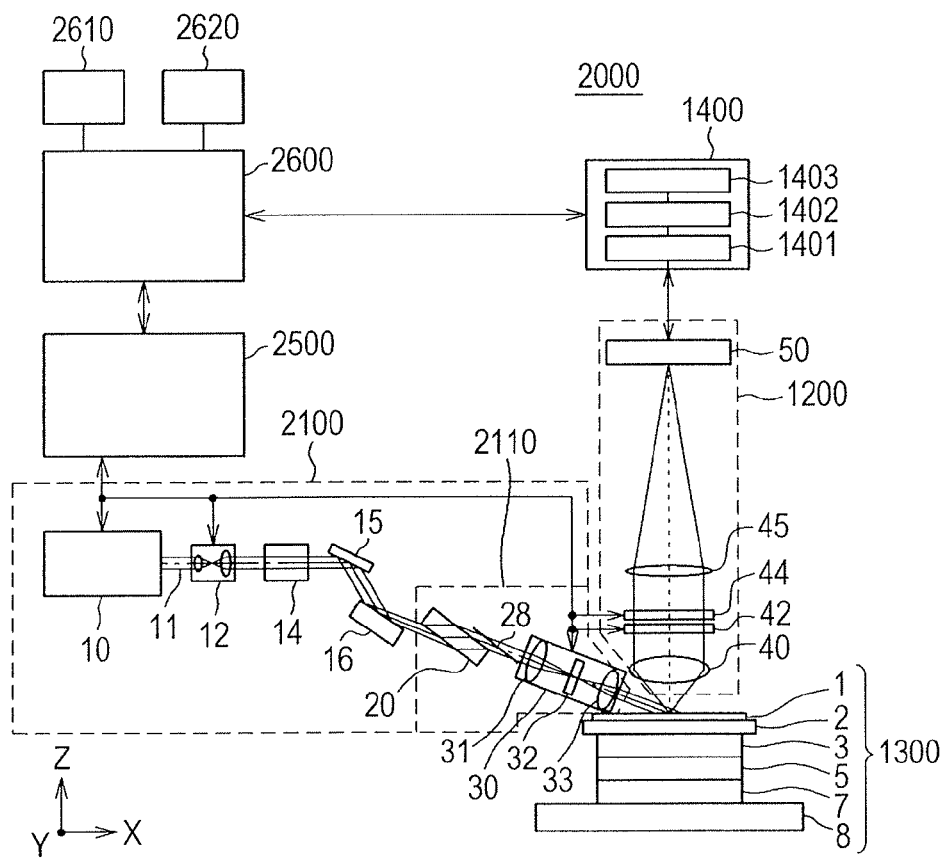
FIG. 6 is a block diagram illustrating a schematic configuration of a defect inspection device in a second embodiment.

FIG. 6 illustrates a schematic configuration of a defect inspection device 2000 including an illumination optical system 2100 which obliquely illuminates above the wafer 1 without using the transmission diffraction gratins 25 and 26 described in the first embodiment or the reflection diffraction grating 29.

The constituent elements, except the illumination optical system 2100, are the same as that of the defect inspection device 1000 described in FIG. 1. Thus, the same reference numerals as those of FIG. 1 are given thereto, and will not be described again.

Figure 7A:
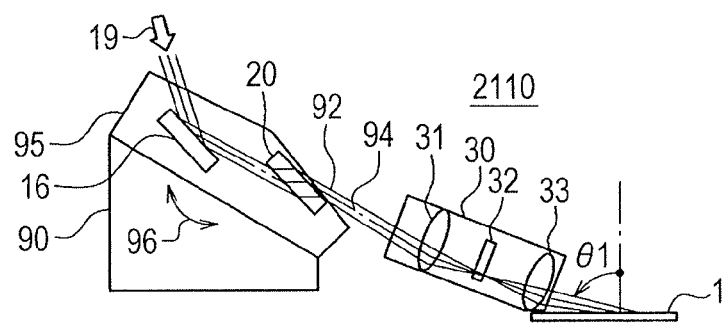
FIG. 7A is a block diagram illustrating a configuration of a beam irradiation unit, when an incident angle of illumination light to a wafer is set to θ3, in the second embodiment.

In the illumination optical system 2100, the laser beam 11 oscillated by the laser light source 10 is expanded into a predetermined beam diameter by the beam expander 12, and it is expanded only in a particular direction by the anamorphic prism 14, thereby being formed in an elliptic light flux. In this case, the particular direction implies a direction in which the condensing of light is performed on the wafer 1. The laser beam 19 which is formed in an elliptic light flux is reflected on the mirrors 15 and 16, and enters a beam irradiation unit 2110. The laser beam 19 having an elliptic light flux and entered the beam irradiation unit 2110 enters the cylindrical lens 20 which is arranged with respect to the planar mirror 16, as illustrated in FIG. 7A. The laser beam 10 transmitted through the cylindrical lens 20 will be a narrow light flux one direction of which is condensed, to form a linearly condensed light image 92 (intermediate image). To obtain a narrower condensed width by reducing the aberration in the linear condensed light image 92, it is preferred that the convex surface of the cylindrical lens 20 has an aspherical surface form.

The light which has formed the linear condensed light image 92 enters a relay lens 30 having the lenses 31 and 33 and a zoom function, and the linear condensed light image 92 is obliquely formed in the linear region 35 on the wafer 1. The linear region 35 on the wafer 1 is longitudinal in the X direction and narrow in the Y direction. The linear region 35, to which the illumination light is irradiated on the wafer 1, is longitudinal in the X direction. By setting the relay lens 30 in a manner that the surface of the wafer 1 and the linearly condensed light 35 are in a conjugate relationship, the linearly condensed light 92 formed by the cylindrical lens 20 is projected and illuminated in the linear region 35 on the wafer 1.

When there is set a large incidence angle of the condensed illumination light irradiated into the linear region 35 on the wafer 1 from the relay lens 30, the incidence angle of the laser beam 19 entering the cylindrical lens 20 after reflected on the planar mirror 16 is large as well. In this case, to reduce the reflection loss on the surface of the cylindrical lens 20, the polarization of the laser beam 19 entering the cylindrical lens 20 is selected as S polarization light or P polarization light, and an antireflection film (not illustrated) to be formed on the surface of the cylindrical lens 20 is necessarily optimized. The polarization light for restraining the surface reflection is assumed as incidence polarization light toward the cylindrical lens 20 where a non-illustrative antireflective film is formed. However, to visualize defects generated on the wafer 1, it is necessary to be able to change the polarization state of the light between S/P/circular polarization in accordance with the defect type. A wavelength plate 32 is embedded into the relay lens 30. The plate 32 is formed of a ½ wavelength plate, a ¼ wavelength plate, or a combination thereof, which is independently rotatable.

Figure 7B:
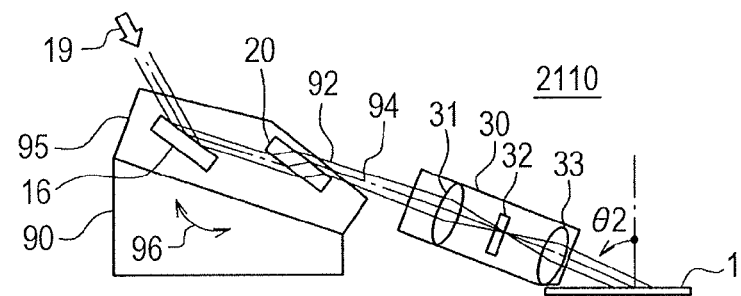
FIG. 7B is a block diagram illustrating a configuration of the beam irradiation unit, when an incident angle of illumination light to a wafer is set to θ4, in the second embodiment.

FIG. 7A and FIG. 7B illustrate a unit for changing an elevation angle of illumination light (illumination elevation angle) entering the wafer 1. The planar mirror 16 and the cylindrical lens 20 form a light condensing unit 95, and this unit has an integral structure. FIG. 7A illustrates a case of a large incidence angle θ3 toward the wafer 1, while FIG. 7B illustrates a case of a small incidence angle θ4. In FIG. 7A, the light condensing unit 95 which is formed of the planar mirror 16 and the cylindrical lens 20 is mounted on a goniometer 90.

The elliptical light flux 19 entering the light condensing unit 95 after reflected on the planar mirror 15 is reflected on the planar mirror 16, and enters the cylindrical lens 20. The elliptical light flux 19 emitted from the cylindrical lens 20 is condensed in one direction, thereby forming the linearly condensed light image 92. The goniometer 90 can rotate the light condensing unit 90, at, as a rotation center, an intersection 94 between this linearly condensed light 92 and the optical axis of the elliptical light flux 19 emitted from the cylindrical lens 20. The light having formed the linear condensed light image 92 enters the relay lens 30 including a zoom function, and is irradiated into the linear region 35 in the surface of the wafer 1 where the entire area of the linearly condensed light image 92 and the surface of the wafer 1 are in a conjugate relationship.

In the configuration illustrated in FIG. 7B, the light condensing unit 95 rotates (in a counter clockwise direction on the illustration sheet), thereby rotating a linearly condensed light image 92 as well. At this time, a beam of light forming the linearly condensed light image 92 is inclined in a direction that the angle formed with the Z axis gets large. As a result, the light transmitting through the zoom lens has the small incidence angle θ4 on the wafer 1.

Because the linearly condensed light image 92 rotates, the linearly condensed light image 92 and the wafer 1 are not conjugate with each other, at the magnification same as the magnification of the relay lens 30 including the zoom function of FIG. 7A. Thus, the magnification of the relay lens 30 including the zoom function (configuration for realizing the zoom function is not illustrated) is adjusted and reduced from the case of FIG. 7A. This magnification is adjusted for projecting the linearly condensed light image 92 on the wafer 1. As a result, the linearly condensed light image 92 and the wafer 1 can be in a conjugate relationship.

Figure 8:
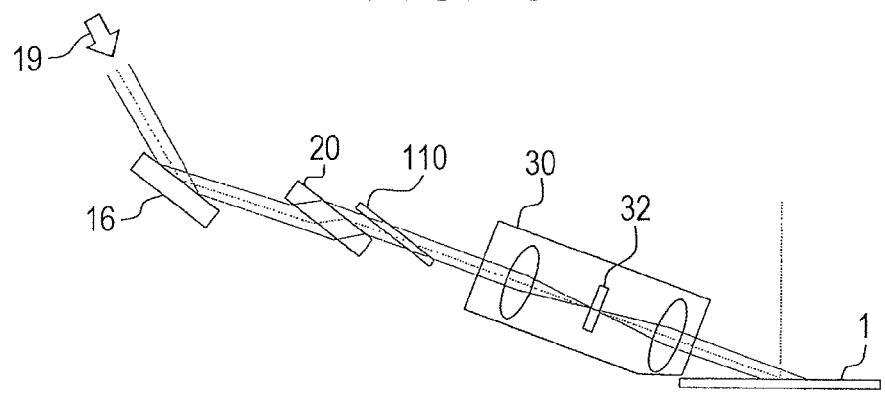
FIG. 8 is a block diagram illustrating a configuration of the beam irradiation unit, having a slit for transmitting a image of light condensed by a cylindrical lens in a position for forming the image of the condensed light, as a first modification of the beam irradiation unit in the second embodiment.

FIG. 8 illustrates a configuration for mechanically forming a narrow form, for oblique projection on the wafer 1, as the first modification of the second embodiment. The configuration of the optical system is the same as that illustrated in FIG. 6, and a slit plate 110 having a linear opening 113 is arranged in a position for linearly condensing light by the cylindrical lens 20. The image of the opening 113 in the slit plate 110 is obliquely projected on the wafer 1 using the relay lens 30. As a result, it is possible to restrain a change in the linearly illumination position or line width due to the fluctuation of the laser beam.

Figure 9A:
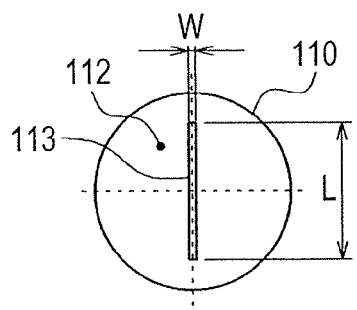
FIG. 9A is a front view of a slit plate.
Figure 9B:
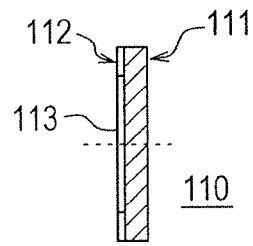
FIG. 9B is a side view of the slit plate.

FIG. 9A illustrates a front view of a structure of the slit plate 110, while FIG. 9B is a side view of the slit plate. A substrate 111 of the slit plate 110 is formed of synthesis silica through which ultraviolet light transmits. A reflecting film or an absorbing film is formed for a light shielding unit 112, while any of these films is not formed for the slit-like formed opening 113 (width W, length L). Candidates of the reflection film 113 formed for the light shielding unit 112 include a dielectric multilayer and a metal film such as aluminum, while a candidate of the absorbing film is chromium oxide. The opening width W of the opening 113 illustrated in FIG. 9A is in a range from 2 to 1 μm. Thus, it is possible to form an opening pattern using a photolithography process and an etching process.

Figure 10A:
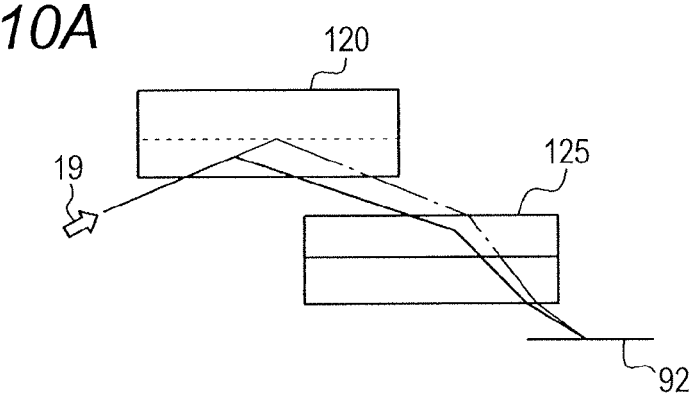
FIG. 10A is a front view of a beam irradiation unit which is formed of a concave mirror and a convex mirror, as a second modification of the beam irradiation unit in the second embodiment.

FIG. 10A illustrates a unit for forming the linearly condensed light image 92 to be projected on the wafer 1 using the relay lens 30 or the relay lens 30 having the zoom function, as the second modification of the second embodiment. The parallel light 19 which is elliptically formed is caused to enter a concave cylindrical mirror 120, and this reflected light is caused to enter a convex cylindrical lens 125, thereby forming the linearly condensed light image 92. The convex cylindrical lens 125 is formed to have the convex surface radius which is approximately one half of the radius of the reflecting surface of the concave cylindrical mirror 120. As a result, it is possible to condense the beams of light in directions orthogonal to the concave cylindrical mirror 120 and the plane of incidence of the convex cylindrical lens 125. As a result, the longitudinal direction of the linearly condensed light image 92 is not expanded more than necessary, thus avoiding a reduction in the illumination efficiency.

Figure 10B:
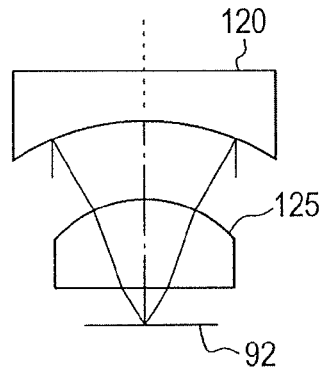
FIG. 10B is a side view of a beam irradiation unit which is formed of a concave mirror and a convex mirror, as a second modification of the beam irradiation unit in the second embodiment.

As shown in FIG. 10B, at least one of the concave surface of the concave cylindrical mirror 120 and the convex surface of the cylindrical lens 125 has an aspherical form. As a result, it is possible to reduce the aberration in the formation position of the linearly condensed light image, thus attaining a very small width of condensing light. An alternative solution for that is wavefront correction in a manner that the aberration is reduced with another optical element, even if the concave surface or the convex surface is not formed to have an aspherical form. For example, the planar mirror 15 of FIG. 6 has an aspherical form, or one surface of a parallel plate (not illustrated) has an aspherical form.

Third Embodiment

Figure 11A:
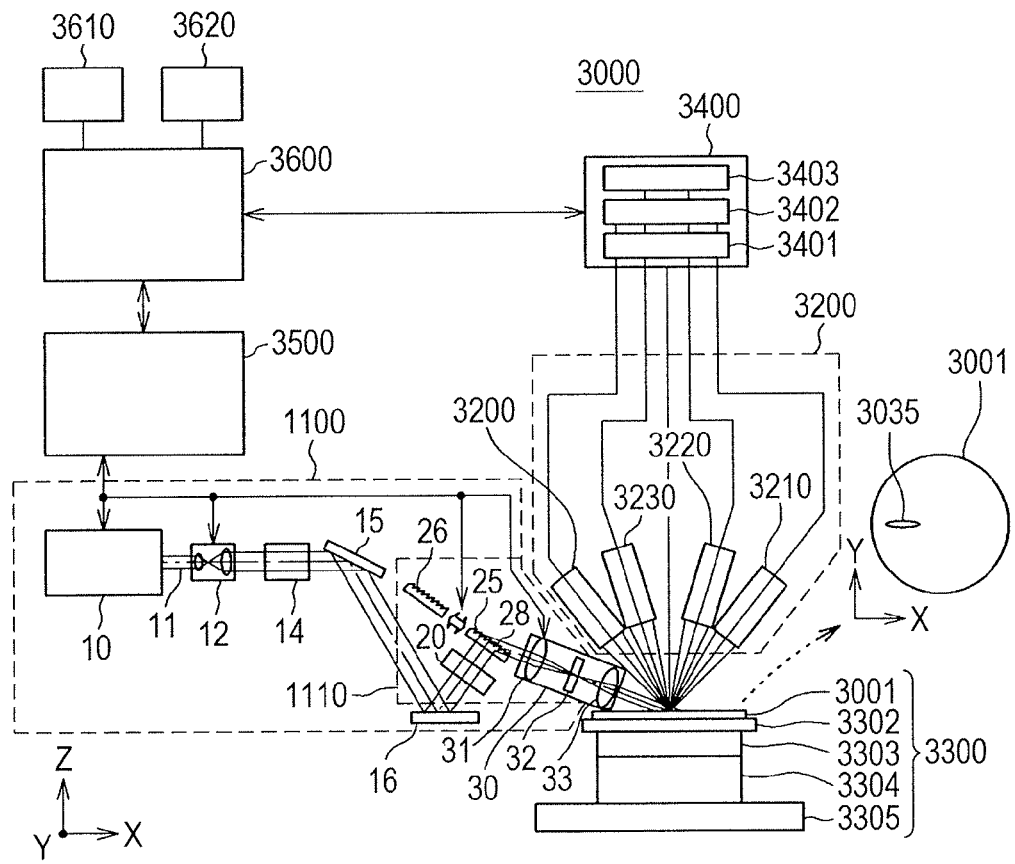
FIG. 11A is a block diagram illustrating a schematic configuration of a defect inspection device according to a third embodiment.

Descriptions will now be made to an example in which the present invention is applied to a surface inspection device which detects surface defects or foreign matters attached on the surface on a wafer (bear wafer) where no pattern is formed thereon, using FIG. 11A. In FIG. 11A, the same constituent elements as those of FIG. 1 descried in the first embodiment are identified with the same reference numerals as those in FIG. 1.

The surface inspection device illustrated in FIG. 11A includes the illumination optical system 1100, a detecting optical system 3200, a stage unit 3300, an image processing unit 3400, a mechanism control unit 3500, an entire control unit 3600, a storage unit 3610, and a display unit 3620.

In the above configuration, the illumination optical system 1100 has the same configuration as that of the first embodiment. An image of light, which is linearly condensed on the surface of the transmission diffraction grating 25 by the cylindrical lens 20, is obliquely projected and formed in a linear region 3035 on the surface of a wafer 3001 through the relay lens 30.

The detecting optical system 3200 detects scattered light generated in the linear region 3056 on the surface of the wafer 3001, on which the image of illumination light which is linearly condensed is obliquely projected.

The wafer 3001 is chucked by a chuck 3302 of the stage unit 3300. It includes a θ stage 3303, an X stage 3304, and a base plate 3305. The θ stage 3303 lets the chuck 3302 rotate thereon. The X stage 3304 accepts the θ stage 3303 to be mounted thereon, and is movable in an X direction. The base plate 3305 accepts the X stage 3304 to be mounted thereon. The stage unit 3300 includes a sensor for detecting the rotational angle of the θ stage 3303 and a sensor for detecting the position of the X stage. These sensors are not illustrated.

An image of illumination light which is linearly condensed is obliquely projected in the linear region 3035 of the surface of the wafer 3001, in a state where the wafer 3001 is chucked by the chuck 3302, rotated by the θ stage 3303, and moved by the X stage 3304 at a constant speed in the X direction during rotation.

The detecting optical system 3200 includes low angle scattered light detecting optical systems 3210 and 3240 and high angle scattered light detecting optical systems 3220 and 3230. The low angle scattered light detecting optical systems 3210 and 3240 detect light scattered in a low angle direction as seen from the surface of the wafer 3001, of scattered light generated in the linear region 3035 on the surface of the wafer 3001. The high angle scattered light detecting optical systems 3220 and 3230 detect light scattered in a high angle direction as seen from the surface of the wafer 3001.

Figure 11B:
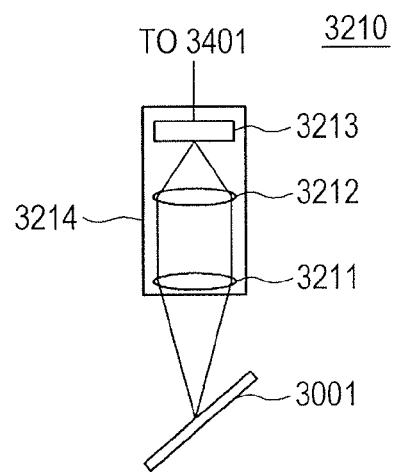
FIG. 11B is a cross sectional view illustrating a schematic configuration of a low angle scattered light detecting optical system of a detecting optical system of a defect inspection device in an third embodiment.

As illustrated in FIG. 11B, the configuration of the low angle scattered light detecting optical system 3210 includes an objective lens 3211, an image forming lens 3212, a one-dimensional sensor 3213, and a lens-barrel 3214. The objective lens 3211 condenses light scattered in a direction of the low angle scattered light detecting optical system 3210, of scattered light generated in the linear region 3035 on the surface of the wafer 3001. The image forming lens 3212 forms an image of the scattered light in the linear region 3035 on the surface of the wafer 3001, with the scattered light condensed by the objective lens 3211. The one-dimensional sensor 3213 detects the image of the scattered light in the linear region 3035, as formed by the image forming lens 3212. The lens-barrel 3214 includes the entire elements. The low angle scattered light detecting optical system 3240 and the high angel scattered light detecting optical systems 3220 and 3230 also have the same configuration.

An analog signal is obtained, upon detection of the image of the scattered light generated in the linear region 3035 on the surface of the wafer 3001, by each of the low angle scattered light detecting optical systems 3210 and 3240 and the high angle scattered light detecting optical systems 3220 and 3230. This obtained analog signal is input and amplified by the A/D conversion unit 3401 of the image processing unit 3400, thereafter being converted into a digital signal (A/D conversion). The A/D converted signal is processed by a signal processing unit 3402 to obtain an image signal. The image signal is processed by a defect detecting unit 3403, to detect defect candidates on the wafer 3001 and to extract feature amounts of the defects detected on the wafer 3001 including position information, size, length, and the brightness of the image.

The detected position information of the defect candidates or the feature amount information are sent to the entire control unit 3600. The processes by the entire control unit 3600 and the functions of the mechanism control unit 3500 are the same as the processes by the system control unit 1600 and the functions of the mechanism control unit 1500 explained in the first embodiment, and thus will not be described again.

In a surface inspection device 3000 having the above configuration, the illumination optical system 1100 forms an image of condensed light with the laser beam 19 which is linearly condensed by the cylindrical lens 20 in the linear region 3035 on the wafer 3001. Thus, it is possible to realize the width of the linear region 3035 for forming the image on the wafer 3001, in a range from 1 to 2 μm or ever thinner than that, regardless of the incidence angle of the illumination light for the wafer 3001, as long as an image of condensed light with a width from 1 to 2 μm or thinner can be formed by the cylindrical lens 20. As a result, it is possible to avoid diffusion of illumination light to a region, having nothing to do with inspection and beyond the image range for inspection, and to efficiently irradiate the laser beam output from the laser light source 10 onto a region for inspection on the wafer 3001, that is, the imaging range for inspection. As a result, it is possible to improve the illumination brightness of the linear region which has a narrow line width and to which the illumination light is irradiated, on the wafer 3001. This enables high sensitive inspection.

Fourth Embodiment

Figure 12:
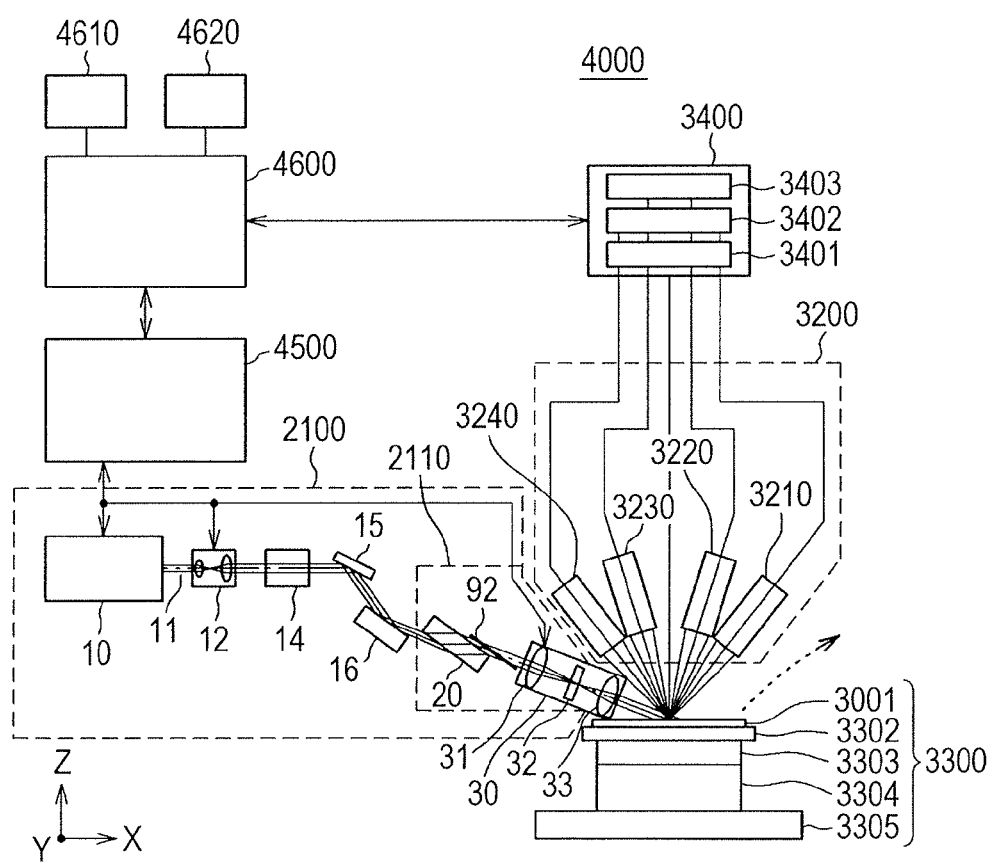
FIG. 12 is a block diagram illustrating a schematic configuration of a defect inspection device in a fourth embodiment.

Descriptions will now be made to an example using FIG. 12 in which the illumination optical system described in the second embodiment is applied to a surface inspection device 4000 which detects surface defects or foreign matters attached on a surface of the wafer (bear wafer) 3001 where no patter is formed on the surface. In FIG. 12, the same reference numerals are given to those constituent elements same as those of FIG. 6 described in the second embodiment or those of FIG. 11A described in the third embodiment.

The surface inspection device illustrated in FIG. 12 includes the illumination optical system 2100, the detecting optical system 3200, the stage unit 3300, an image processing unit 4400, a mechanical control unit 4500, an entire control unit 4600, a storage unit 4610, and a display unit 4620.

In the above configuration, the illumination optical system 2100 has the same configuration described in the second embodiment. The image of the illumination light 92 linearly condensed by the cylindrical lens 20 is obliquely projected and formed in the linear region 3035 on the surface of the wafer 3001 through the relay lens 30.

As described in the second embodiment, the planar mirror 16 and the cylindrical lens 20 of the illumination optical system 2100 are mounted on the goniometer 90, at, as a rotation center, a position where the image of the illumination image 92 linearly condensed by the cylindrical lens 20 is formed. This is not illustrated in FIG. 12.

The detecting optical system 3200 detects the light scattered in the linear region 3035 on the surface of the wafer 3001, onto which the image of the linearly condensed illumination light is obliquely protected.

The operations from the signal processing for a signal detected by the detecting optical system 3200 are the same as those described in the third embodiment, and thus will not be described again.

Accordingly, the descriptions have specifically been made to the present invention of the present inventors. However, the present invention is not limited to the above embodiments, and various modifications are included. For example, a configuration part of some embodiment may be replaced with another configuration part of another embodiment, or a configuration part of some embodiment may be added to another configuration, without departing from the scope. A configuration part of each embodiment may be added to, deleted from, and replaced with another known configuration.

DESCRIPTION OF SYMBOLS

1,3001 . . . wafer 2,3302 . . . chuck 3 . . . z stage 3303 . . . θ stage 5,3304 . . . x stage 7 . . . y stage 8,3305 . . . base plate 10 . . . laser light source 12 . . . beam expander 14 . . . anamorphic prism 20 . . . cylindrical lens 25 . . . transmission diffraction grating 29 . . . reflection diffraction grating 30 . . . relay lens 32 . . . wavelength plate 1200,3200 . . . detection optical system 40,3211 . . . objective lens 42 . . . spatial filter 44 . . . polarization filter 45,3212 . . . imaging lens 50,3213 . . . image sensor 1300,3300 . . . stage unit 1400,3400 . . . image processing unit 1600,2600,3600,4600 . . . system control unit 1500, 2500,3500,4500 . . . mechanism control 110 . . . slit 120 . . . concave cylindrical mirror 125 . . . convex cylindrical mirror

What is claimed is:

1. A defect inspection device, comprising:
   a table unit on which a target sample to be inspected is mounted;
   an illumination optical system unit configured to obliquely illuminate the sample mounted on the table unit;
   a detecting optical system unit which condenses scattered light generated from the sample on which illumination light is obliquely irradiated by the illumination light optical system unit, and detects an image on a surface of the sample using the scattered light;
   an image processing unit configured to process a signal obtained by detecting the image on the surface of the sample using the scattered light by the detecting optical system unit, to extract defect candidates on the surface of the sample; and
   a control unit which controls the table unit, the illumination optical system unit, the detecting optical system unit, and the image processing unit,
   wherein the illumination optical system unit includes
   a laser light source which emits a laser beam;
   a beam expander which expands a diameter of the laser beam;
   an anamorphic optical unit which controls a size of the laser beam in a particular direction;
   a cylindrical optical unit which condenses the laser beam passed through the anamorphic optical unit in one direction and forms a linearly condensed light image as an intermediate image; and
   a relay lens unit which forms the linearly condensed light image on a surface of the specimen mounted on the table unit to illuminate a linear region on the specimen,
   wherein a polarization condition of the laser beam passing through the anamorphic optical unit and the cylindrical optical unit is a specific linearly polarized condition,
   wherein optical coatings are applied to surfaces of a cylindrical lens of the cylindrical optical unit, said optical coatings corresponding to the polarization state of the laser beam to reduce power loss of the laser beam, and
   wherein the relay lens unit includes a polarization control element which controls polarization condition of the laser beam illuminating the specimen.

2. The defect inspection device according to claim 1, wherein
   light emitted from the light source from an anamorphic prism of the anamorphic optical unit is formed as an ellipse in cross section perpendicular to an optical axis of said emitted light, and
   the elliptic light is caused to enter the cylindrical lens.

3. The defect inspection device according to claim 1, wherein
   the cylindrical lens has a convex surface, and
   the convex surface has an aspherical surface form.

4. The defect inspection device according to claim 1,
   wherein the illumination optical system unit further includes a diffraction grating, and
   wherein the illumination optical system unit condenses light linearly on the cylindrical optical unit to form an image of the condensed light on a surface of the diffraction grating,
   condenses high-order diffracted light by the relay lens unit, of diffracted light generated by the diffraction grating on which the image of the condensed light is formed, and
   forms a pattern of the image of the condensed light by the condensed high-order diffracted light on the surface of the sample.

5. The defect inspection device according to claim 4, wherein the illumination optical system unit includes a plurality of diffraction gratings with different pattern pitches in the diffraction gratings, and switches the diffraction gratings arranged in a position for forming the image of the light condensed linearly by the cylindrical lens, thereby changing an incidence angle of the image of the condensed light to be formed on the surface of the sample.

6. The defect inspection device according to claim 1, wherein the detecting optical system unit detects the image on the surface of the sample using the scattered light which is scattered above including a direction perpendicular to the surface of the sample, of scattered light generated in a linear region on the surface of the sample illuminated with the illumination light.

7. The defect inspection device according to claim 1, wherein the detecting optical system unit includes:
   a high angle scattered light detecting system detecting the image on the surface of the sample with the scattered light scattered in a high angle direction with respect to the surface of the sample of the scattered light generated in a linear region of the surface of the sample illuminated with the illumination light, and
   a low angle scattered light detecting system detecting the image on the surface of the sample with the scattered light scattered in a low angle direction with respect to the surface of the sample of the scattered light generated in a linear region of the surface of the sample illuminated with the illumination light, and wherein the image processing unit extracts defect candidates on the surface of the sample, using a detection signal of the image detected by the high angle scattered light detecting system, on the surface of the sample with the scattered light scattered in the high angle direction, and a detection signal of the image detected by the low angle scattered light detecting system, on the surface of the sample with the scattered light scattered in the low angle direction.

8. A defect inspection method, comprising the steps of:

irradiating illumination light obliquely onto a sample mounted on a table which is continuously moved in one direction;

detecting an image on a surface of the sample using scattered light, by condensing the scattered light generated on the sample onto which the illumination light is obliquely irradiated; and processing a signal obtained by detecting the image on the surface of the sample using the scattered light to extract defect candidates on the surface of the sample, wherein said irradiating the illumination light obliquely onto the sample includes emitting a laser beam from a laser light source;

expanding a diameter of the laser beam with a beam expander;

controlling a size of the laser beam in a particular direction with an anamorphic optical unit;

condensing the laser beam passed through the anamorphic optical unit in one direction and forming a linearly condensed light image as an intermediate image with a cylindrical optical unit; and forming the linearly condensed light image on a surface of the specimen mounted on the table to illuminate a linear region on the specimen with a relay lens unit, wherein a polarization condition of the laser beam passing through the anamorphic optical unit and the cylindrical optical unit is a specific linearly polarized condition, wherein power loss of the laser beam is reduced by optical coatings corresponding to a polarization state of the laser beam, the optical coatings being applied to surfaces of a cylindrical lens of the cylindrical optical unit, and wherein a polarization condition of the laser beam illuminating the specimen is controlled by a polarization control element included in the relay lens unit.

9. The defect inspection method according to claim 8, wherein the irradiating the illumination light obliquely onto the sample includes:

forming the light emitted from the light source as an ellipse in cross section perpendicular to an optical axis of the light, and forming an image of condensed light by linearly condensing the light which is formed as an ellipse.

10. The defect inspection method according to claim 8, further comprising:

forming the image of the condensed light on a surface of a diffraction grating;

condensing high-order diffracted light, of diffracted light generated by the diffracted grating having the surface on which the image of the condensed light is formed; and forming a pattern of the image of the condensed light using the condensed high-order diffracted light on the surface of the sample.

11. The defect inspection method according to claim 10, further comprising the step of:

switching the diffraction grating for forming the image of condensed light with a diffraction grating having a patch different from a pitch of a grating pattern formed in the diffraction grating, thereby changing an incidence angle to the surface of the sample of the high-order diffracted light to be formed on the surface of the sample.

12. The defect inspection method according to claim 8, wherein the table is continuously moved in one direction while being rotated.

13. The defect inspection method according to claim 8, wherein the detecting the image on the surface of the sample using the scattered light is performed by detecting the image on the surface of the sample using scattered light scattered above including a direction perpendicular to the surface of the sample, of scattered light generated in a linear region of the surface of the sample onto which the illumination light is irradiated.

14. The defect inspection method according to claim 8, wherein the detecting the image on the surface of the sample using the scattered light includes detecting the image on the surface of the sample using scattered light scattered in a high angle direction with respect to the surface of the sample and the image on the surface of the sample using scattered light scattered in a low angle direction with respect to the surface of the sample, of scattered light generated in the linear region of the surface of the sample onto which the illumination light is illuminated, and the extracting the defect candidates on the surface of the sample includes extracting the defect candidates on the surface of the sample, using a detection signal of the image on the surface of the sample using the scattered light scattered in the high angle direction and a detection signal of the image on the surface of the sample using the scattered light scattered in the low angle direction.

15. The defect inspection device according to claim 1, wherein an elevation angle of the illumination optical system for illuminating the specimen is changeable.

16. The defect inspection device according to claim 1, wherein the illumination optical system unit further comprises a slit plate having a slit-like opening disposed in a position on which the linearly condensed light image or intermediate image is formed.

17. The defect inspection device according to claim 1, wherein the cylindrical optical unit includes a cylindrical mirror having a concave reflection surface and the cylindrical lens having a convex surface.

18. The defect inspection method according to claim 8, wherein an elevation angle of the illumination optical system for illuminating the specimen is changeable.

19. The defect inspection method according to claim 8, wherein the linearly condensed light image or intermediate image passes through a slit-like opening formed on a slit plate which is disposed in a position on which the linearly condensed light image or intermediate image is formed.

20. The defect inspection method according to claim 8, wherein the linearly condensed light image is formed on the surface of the specimen by a cylindrical mirror having a concave reflection surface and the cylindrical lens having a convex surface, the cylindrical mirror being in the cylindrical optical unit.

* * * * *